United States Patent
Feng et al.

(10) Patent No.: US 12,357,846 B2
(45) Date of Patent: Jul. 15, 2025

(54) BEAM STOPPER FOR A RADIOTHERAPY DEVICE

(71) Applicant: ELEKTA BEIJING MEDICAL SYSTEMS CO., LTD, Beijing (CN)

(72) Inventors: Xun Feng, Beijing (CN); Yingping Zhao, Beijing (CN); Shijia Zhang, Beijing (CN)

(73) Assignee: ELEKTA BEIJING MEDICAL SYSTEMS CO., LTD, Beijing (CN)

( * ) Notice: Subject to any disclaimer, the term of this patent is extended or adjusted under 35 U.S.C. 154(b) by 166 days.

(21) Appl. No.: 17/757,682

(22) PCT Filed: Nov. 26, 2020

(86) PCT No.: PCT/CN2020/131937
§ 371 (c)(1),
(2) Date: Jun. 17, 2022

(87) PCT Pub. No.: WO2021/121005
PCT Pub. Date: Jun. 24, 2021

(65) Prior Publication Data
US 2023/0025744 A1    Jan. 26, 2023

(30) Foreign Application Priority Data
Dec. 19, 2019 (CN) .......................... 201911320934.2

(51) Int. Cl.
*A61N 5/10* (2006.01)
(52) U.S. Cl.
CPC ......... *A61N 5/1048* (2013.01); *A61N 5/1081* (2013.01); *A61N 2005/1094* (2013.01)

(58) Field of Classification Search
CPC ....... A61B 6/107; A61B 6/4092; A61B 6/035; A61N 2005/1094; A61N 5/1048; A61N 5/1081; A61N 5/1077
See application file for complete search history.

(56) References Cited

U.S. PATENT DOCUMENTS

| | | |
|---|---|---|
| 629,658 A | 7/1899 | Cargill |
| 2,217,783 A | 10/1940 | Bell |

(Continued)

FOREIGN PATENT DOCUMENTS

| | | |
|---|---|---|
| CN | 106456991 A | 2/2017 |
| CN | 108325093 A | 7/2018 |

(Continued)

OTHER PUBLICATIONS

"U.S. Appl. No. 17/757,674 Preliminary Amendment Filed with Application", 8 pgs.

(Continued)

Primary Examiner — David J Makiya
Assistant Examiner — Soorena Kefayati
(74) Attorney, Agent, or Firm — Schwegman Lundberg & Woessner, P.A.

(57) ABSTRACT

A radiotherapy system (220, 320) comprises a first rotary support apparatus (204, 304) configured to support a radiation beam source (200, 300) and to cause a radiation beam source (200, 300) to rotate about a rotation axis (218, 318, 518), a second rotary support apparatus (214, 314, 414, 514) and a radiation shield (202, 302, 402, 502) mounted to the second rotary support apparatus (214, 314, 414, 514). The second rotary support apparatus (214, 314, 414, 514) is configured to cause the radiation shield (202, 302, 402, 502) to rotate about the rotation axis (218, 318, 518).

25 Claims, 8 Drawing Sheets

(56) References Cited

U.S. PATENT DOCUMENTS

| | | | |
|---|---|---|---|
| 3,259,921 | A | 7/1966 | Alsobrook, Jr. |
| 3,885,556 | A | 5/1975 | Agatani |
| 3,991,428 | A | 11/1976 | Hanson |
| 4,195,829 | A | 4/1980 | Reser |
| 4,356,577 | A | 11/1982 | Taylor et al. |
| 4,613,122 | A | 9/1986 | Manabe |
| 4,618,133 | A | 10/1986 | Siczek |
| 4,715,073 | A | 12/1987 | Butler |
| 4,856,129 | A | 8/1989 | Butler |
| 5,199,123 | A | 4/1993 | Jacques et al. |
| 5,208,928 | A | 5/1993 | Kuck et al. |
| 5,237,600 | A | 8/1993 | Kamata |
| 5,402,544 | A | 4/1995 | Crawford et al. |
| 5,490,297 | A | 2/1996 | Bradcovich et al. |
| 5,596,779 | A | 1/1997 | Meek |
| 5,619,763 | A | 4/1997 | Randolph et al. |
| 5,802,639 | A | 9/1998 | Raasch et al. |
| 5,903,940 | A | 5/1999 | Voelker et al. |
| 5,937,459 | A | 8/1999 | Binaghi et al. |
| 5,940,911 | A | 8/1999 | Wang |
| 6,094,760 | A | 8/2000 | Nonaka et al. |
| 6,240,582 | B1 | 6/2001 | Reinke |
| 6,615,429 | B2 | 9/2003 | Weil et al. |
| 6,640,363 | B1 | 11/2003 | Pattee et al. |
| 6,678,907 | B1 | 1/2004 | Voelker et al. |
| 6,681,423 | B2 | 1/2004 | Zachrisson |
| 6,772,462 | B1 | 8/2004 | Harrell |
| 6,957,456 | B2 | 10/2005 | Darling et al. |
| 8,056,163 | B2 | 11/2011 | Lemire et al. |
| 8,096,007 | B2 | 1/2012 | Dyreby et al. |
| 9,113,804 | B2 | 8/2015 | Kimishima |
| 10,695,586 | B2 * | 6/2020 | Harper ................ A61N 5/1081 |
| 12,285,634 | B2 | 4/2025 | Eldered et al. |
| 2002/0077525 | A1 | 6/2002 | Costanzo |
| 2003/0146425 | A1 | 8/2003 | Drake et al. |
| 2004/0098804 | A1 | 5/2004 | Varadharajulu et al. |
| 2004/0261176 | A1 | 12/2004 | Plannerer |
| 2005/0223491 | A1 | 10/2005 | Mccrimmon |
| 2006/0193443 | A1 | 8/2006 | Reger |
| 2007/0023066 | A1 | 2/2007 | Yokokawa et al. |
| 2007/0226906 | A1 | 10/2007 | Farooqui |
| 2007/0230660 | A1 | 10/2007 | Herrmann |
| 2008/0086816 | A1 | 4/2008 | Farooqui |
| 2010/0104159 | A1 | 4/2010 | Hirokawa et al. |
| 2010/0199433 | A1 | 8/2010 | Clenet |
| 2010/0280549 | A1 | 11/2010 | Yen |
| 2011/0199085 | A1 | 8/2011 | Allen et al. |
| 2011/0209286 | A1 | 9/2011 | Dane |
| 2011/0211665 | A1 * | 9/2011 | Maurer, Jr. .......... A61N 5/1039 378/19 |
| 2011/0313228 | A1 | 12/2011 | Handa et al. |
| 2012/0150018 | A1 | 6/2012 | Yamaya et al. |
| 2013/0111668 | A1 | 5/2013 | Wiggers et al. |
| 2013/0158382 | A1 * | 6/2013 | Chao ................... A61N 5/1081 600/407 |
| 2013/0227787 | A1 | 9/2013 | Herbst et al. |
| 2013/0259209 | A1 | 10/2013 | Goto et al. |
| 2014/0171725 | A1 * | 6/2014 | Adler ..................... G21F 3/00 600/1 |
| 2014/0275697 | A1 | 9/2014 | Filiberti |
| 2015/0190295 | A1 | 7/2015 | Tso et al. |
| 2015/0285430 | A1 | 10/2015 | Wang |
| 2015/0352373 | A1 * | 12/2015 | Subrahmanyam ... A61N 5/1081 600/1 |
| 2016/0000620 | A1 | 1/2016 | Koch |
| 2016/0095558 | A1 | 4/2016 | Choy et al. |
| 2016/0331613 | A1 | 11/2016 | Lee et al. |
| 2017/0095219 | A1 | 4/2017 | Wakahara |
| 2017/0258414 | A1 | 9/2017 | Guertin et al. |
| 2017/0319410 | A1 | 11/2017 | Lee |
| 2017/0340903 | A1 * | 11/2017 | Ie ......................... A61B 6/4452 |
| 2018/0078223 | A1 | 3/2018 | Oishi |
| 2018/0085603 | A1 | 3/2018 | Kruesi et al. |
| 2018/0133518 | A1 * | 5/2018 | Harper ................. A61N 5/1049 |
| 2018/0147105 | A1 | 5/2018 | Timm et al. |
| 2018/0154183 | A1 * | 6/2018 | Sahadevan .......... A61M 1/3615 |
| 2018/0280733 | A1 * | 10/2018 | Weidlich .............. A61B 6/4078 |
| 2018/0339172 | A1 | 11/2018 | Stahl et al. |
| 2019/0368652 | A1 | 12/2019 | Olea |
| 2020/0043624 | A1 * | 2/2020 | Schnarr ............... A61N 5/1045 |
| 2020/0289353 | A1 | 9/2020 | Scherff |
| 2020/0390246 | A1 | 12/2020 | Chen et al. |
| 2021/0031055 | A1 * | 2/2021 | Jiang ..................... A61B 5/055 |
| 2021/0100366 | A1 | 4/2021 | Liu |
| 2021/0186789 | A1 | 6/2021 | Campbell et al. |
| 2022/0339469 | A1 | 10/2022 | Eldered et al. |
| 2023/0028350 | A1 | 1/2023 | Carlander et al. |
| 2023/0031538 | A1 | 2/2023 | Alexis et al. |
| 2023/0111290 | A1 | 4/2023 | Wiberg |

FOREIGN PATENT DOCUMENTS

| | | |
|---|---|---|
| EP | 4076645 | 10/2022 |
| JP | 06224 | 1/1994 |
| JP | 10127793 | 5/1998 |
| JP | 2002325854 | 11/2002 |
| WO | 0232312 | 4/2002 |
| WO | 2007018646 | 2/2007 |
| WO | 2007127970 | 11/2007 |
| WO | WO-2011088399 A1 | 7/2011 |
| WO | 2018093937 | 5/2018 |

OTHER PUBLICATIONS

"U.S. Appl. No. 17/757,678 Preliminary Amendment Filed with Application", 10 pgs.

"United Kingdom Application Serial No. 1918753.3, Examination Report mailed Aug. 23, 2022", 1 pg.

"United Kingdom GB1918757.4, Examination Report under Section 18(3) mailed Dec. 22, 2022", (Dec. 22, 2022), 4 pgs.

"European Application Serial No. 20902566.7, European Search Report dated Jan. 5, 2024", (Jan. 5, 2024), 7 pgs.

"International Application Serial No. PCT/CN2020/131937, International Search Report dated Mar. 1, 2021", (Mar. 1, 2021), 4 pgs.

"International Application Serial No. PCT/CN2020/131937, Written Opinion dated Mar. 1, 2021", (Mar. 1, 2021), 6 pgs.

"International Application Serial No. PCT EP2020 086650, International Search Report dated Jun. 24, 2021", (Jun. 24, 2021), 6 pgs.

"International Application Serial No. PCT EP2020 086650, Written Opinion dated Jun. 24, 2021", (Jun. 24, 2021), 8 pgs.

"United Kingdom Application Serial No. 1918753.3, Examination Report dated Dec. 9, 2020", (Dec. 9, 2020), 3 pgs.

"International Application Serial No. PCT EP2020 086663, International Search Report dated Apr. 14, 2021", (Apr. 14, 2021), 3 pgs.

"International Application Serial No. PCT EP2020 086663, Written Opinion dated Apr. 14, 2021", (Apr. 14, 2021), 5 pgs.

"United Kingdom Application Serial No. 1918757.4, Examination Report dated Jun. 17, 2020", (Jun. 17, 2020), 7 pgs.

"European Application Serial No. 1918757.4, European Search Report dated Jun. 17, 2020", (Jun. 17, 2020), 7 pgs.

"International Application Serial No. PCT EP2020 087307, International Search Report dated Apr. 26, 2021", (Apr. 26, 2021), 3 pgs.

"International Application Serial No. PCT EP2020 087307, Written Opinion dated Apr. 26, 2021", (Apr. 26, 2021), 6 pgs.

"U.S. Appl. No. 17/757,675, Notice of Allowance mailed Dec. 18, 2024", 7 pgs.

"U.S. Appl. No. 17/757,675, Supplemental Notice of Allowability mailed Jan. 3, 2025", 3 pgs.

"U.S. Appl. No. 17/757,678, Response filed Jan. 27, 2025 to Restriction Requirement mailed Nov. 25, 2024", 11 pgs.

"U.S. Appl. No. 17/757,674, Response filed Feb. 14, 2025 to Non Final Office Action mailed Nov. 18, 2024", 12 pgs.

"U.S. Appl. No. 17/757,674, Non Final Office Action mailed Nov. 18, 2024", 22 pgs.

"U.S. Appl. No. 17/757,675, Response filed Nov. 18, 2024 to Non Final Office Action mailed Jul. 18, 2024", 11 pgs.

"U.S. Appl. No. 17/757,678, Restriction Requirement mailed Nov. 25, 2024", 7 pgs.

(56) References Cited

OTHER PUBLICATIONS

"U.S. Appl. No. 17/757,675, Non Final Office Action mailed Jul. 18, 2024", 10 pages.
"U.S. Appl. No. 17/757,674, Restriction Requirement mailed Aug. 7, 2024", 6 pages.
"U.S. Appl. No. 17/757,674, Response filed Oct. 2, 2024 to Restriction Requirement mailed Aug. 7, 2024", 10 pages.
"U.S. Appl. No. 17/757,678, Non Final Office Action mailed Apr. 22, 2025", 24 pgs.

* cited by examiner

BEAM STOPPER FOR A RADIOTHERAPY DEVICE

The present disclosure relates generally to radiotherapy apparatuses and systems. More specifically, the present disclosure relates to a radiation shielding system that is suitable for attenuating a beam of radiation used in a radiotherapy system. More specifically, the present disclosure relates to a radiotherapy system comprising a radiation shield suitable for attenuating a radiation beam emitted by a radiation beam source.

PRIORITY APPLICATIONS

This application is a U.S. National Stage Filing under 35 U.S.C. § 371 from International Application No. PCT/CN2020/131937, filed on Nov. 26, 2020, and published as WO2021/121005 on Jun. 24, 2021, which claims the benefit of priority to Chinese Application No. 201911320934.2, filed on Dec. 19, 2019; the benefit of priority of each of which is hereby claimed herein, and which applications and publication are hereby incorporated herein by reference in their entireties.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour. However, in order to apply a prescribed dose to a tumour or other target region within a subject, the radiation must pass through healthy tissue, irradiating and hence potentially damaging it in the process. Modern radiotherapy treatments provide a safe and relatively small radiation dose to healthy tissue, however it is desirable to minimise the dose received by healthy tissue still further during radiotherapy treatments.

Many different radiotherapy techniques exist, allowing radiation to be applied from different angles, at varying intensities, and for varying time periods. A standard approach to minimising the radiation dose received by healthy tissue surrounding a target region is to direct the radiation toward the target region from a plurality of different angles. This may comprise using different sources of radiation arranged at different angles around the patient, or may comprise rotating a source of radiation around the patient. In either case, each beam of radiation passes through the target region, and therefore a prescribed dose may be built up at the target region. However, importantly, applying the radiation beams at different angles means that the radiation dose applied to healthy tissue is spread over a larger region of healthy tissue, thus reducing the dose received by any one particular unit volume of healthy tissue.

In typical applications of radiotherapy, the ionising radiation may be X-ray or gamma ray frequency electromagnetic waves. It is known that a beam of radiation of this frequency may not be completely attenuated at the target region inside the patient but may instead pass through the target region and healthy tissue on the opposite side of the target region and may exit the body of the patient.

In these situations, it is desirable to provide a radiation shield on the opposite side of the patient's body to the radiation source, i.e. diametrically opposed to the radiation source, in order to attenuate the radiation beam that has exited the patient's body. The radiation shield can block the ionising radiation to prevent the beam from travelling further than the immediate vicinity of the radiotherapy device, thus protecting nearby medical staff from the ionising radiation and preventing the radiation damaging any medical equipment in the vicinity.

It is therefore important to provide a radiation shield which will block ionising radiation from the source. Additionally, it is important that the radiation shield is able to move to be able to block radiation as it applied to the target from different angles. However, the materials required to attenuate a powerful gamma to X-ray beam need to be sufficiently thick and made of a heavy metal, such as tungsten on an alloy of tungsten. It is therefore problematic to provide a moveable radiation shield due to its high weight. Embodiments of the present disclosure seek to address this and other issues encountered in the prior art by providing an improved radiotherapy system.

SUMMARY

Aspects of the present disclosure are set out in the independent claims, and optional features are set out in the dependent claims.

Some aspects of the present disclosure relate to a radiotherapy system comprising a first rotary support apparatus, a second rotary support apparatus, and further comprising a radiation shield mounted to the second rotary support apparatus. The first rotary support apparatus is configured to support a radiation beam source and to cause the radiation beam source to rotate about a rotation axis. The second rotary support apparatus is configured to cause the radiation shield to rotate about the rotation axis.

Other aspects of the disclosure relate to a radiation shield mounted to a second rotary drive apparatus for a radiotherapy system according to the disclosures discussed herein.

In more detail, the radiation shield is configured to rotate about the rotation axis such that the radiation shield travels along a curved path, wherein the curved path is along the circumference of a notional circle centred on the rotation axis. The curved path may be a circular path, in other words the radiation shield may be configured to travel along the full circumference of the notional circle. This means that the radiation shield is configured to rotate through 360° about the circle. Alternatively, the curved path may be a portion of a circular path, in other words the radiation shield may be configured to travel along a part of the circumference of the notional circle, and so the radiation shield is configured to rotate through less than 360°.

Additionally, the first rotary support apparatus is configured to cause a radiation beam source to rotate about a rotation axis in a similar manner to the rotation of the radiation shield about the second axis as described above. Specifically, the first rotary support apparatus is configured to cause a radiation beam source to travel along a curved path along a circumference of a notional circle centred on the rotation axis.

Causing a rotation of the radiation beam source or the radiation shield may comprise any suitable rotary drive system that drives a rotation of the source or shield in accordance with the rotary motion as described above.

In more detail, the first rotary support apparatus may be any suitable apparatus that is configured to support a radiation beam source, and that is further configured to cause a rotation of the radiation beam source about a rotation axis. Similarly, the second rotary support apparatus may be any suitable apparatus that is configured to support a radiation shield, and that is further configured to cause a rotation of the radiation shield about a rotation axis. For example, in some embodiments the first and/or second rotary support apparatuses may be any type of rotating gantry, such as a ring gantry, a drum gantry, or a C-arm gantry. In other embodiments, the first and/or second rotary support apparatuses may be curved guides or tracks. Embodiments of the present disclosure extend to any type of first and second rotary support apparatus that are configured to support a respective radiation beam source and radiation shield and are configured to cause a respective rotation of the radiation beam source and radiation shield about respective radiation axes.

By providing a second rotary support apparatus for causing rotation of the radiation shield that is separate from the first rotary support apparatus that causes rotation of the radiation beam source, the total weight of the radiation shield and radiation beam source is distributed over the first and second rotary support apparatuses, as opposed to both components being mounted on the same rotary support apparatus. Therefore the load on either apparatus is reduced compared to a system in which both the source and shield are supported by the same rotary support apparatus. This system therefore improves load distribution for the source and shield components in a radiotherapy system, and enables simpler and possibly cheaper rotary support apparatuses to be used, since each apparatus needs to support less weight.

In some embodiments, the radiotherapy system further comprises a radiation beam source mounted to the first rotary support apparatus. The radiation bean source may be configured to emit a beam of radiation directed towards the rotation axis.

In some embodiments, the radiation shield is configured to be able to rotate about the rotation axis independently of the rotation of the radiation beam source about the rotation axis. This may be advantageous as this allows for a more adaptable radiotherapy system since the radiation shield isn't fixed in relation to the radiation beam source.

In other embodiments, the radiation shield is configured to be able to rotate about the rotation axis in synchrony with the rotation of the radiation beam source. In these embodiments, the rotation of the radiation shield may be synchronised with the rotation of the radiation beam source such that the radiation shield maintains a fixed position relative to the radiation beam source as the radiation beam source rotates about the rotation axis. Optionally, the rotation of the radiation shield is synchronised with the rotation of the radiation beam source such that the radiation shield is always in the path of a radiation beam emitted from the radiation beam source as the radiation beam source rotates about the rotation axis. Furthermore, the rotation of the radiation shield may be synchronised with the rotation of the radiation beam source such that the radiation shield is always positioned to be diametrically opposed to the radiation beam source as the radiation beam source rotates about the rotation axis. This enables an effective way for the radiation shield to be able to attenuate a beam emitted from the radiation beam source. In these embodiments, the radiotherapy system may further comprise a control system configured to control the rotation of the radiation shield to cause the radiation shield to rotate in synchrony with the radiation beam source. The control system may cause the radiation shield to maintain a fixed position relative to the radiation beam source as the radiation beam source rotates, or may cause the radiation shield to always be diametrically opposed to the radiation beam source.

In more detail, the control system may be configured to control first and second drive systems that drive the rotation of the radiation beam source and radiation shield respectively. The control system may be configured to control one or both of the first and second drive systems such that rotation of the radiation shield and radiation beam source are synchronised, or otherwise maintain a fixed relation (such as diametrically opposed to one another) as they rotate about the rotation axis.

In other embodiments, the radiotherapy system may comprise a rotary coupling system such as an arrangement of gears or pulleys that mechanically couple the rotation of the radiation beam source to the rotation of the radiation shield. In these embodiments, the rotation of the radiation beam source may drive the rotation of the radiation shield via the rotary coupling system. In other words, as the radiation beam source rotates about the rotation axis, rotary forces may be transmitted via the rotary coupling arrangement to drive the rotation of the radiation shield about the rotation axis. Alternatively, rotation of the radiation shield drives rotation of the radiation beam source via the rotary coupling apparatus in a similar manner. In further embodiments, the radiotherapy system may comprise a rotary drive apparatus configured to drive the rotation of one of the radiation beam source and radiation shield.

The rotary coupling apparatus advantageously provides a mechanical coupling between the rotation of the radiation shield and radiation beam source, which provides a means to synchronise the rotation of these components such that the beam source and shield maintain a fixed relation as they rotate (such as always being diametrically opposed to one another).

In some embodiments, the rotation of the radiation beam source about the rotation axis causes the radiation beam source to travel along a first curved path, the first curved path being along at least a portion of a circumference of a circle centred on the rotation axis. Similarly, rotation of the radiation shield about the rotation axis causes the radiation shield to travel along a second curved path, the second curved path being along at least a portion of a circumference of a circle centred on the rotation axis.

In some embodiments, the second rotary support apparatus comprises a rotatable gantry, and the radiation shield is fixed to the gantry. The gantry is configured to rotate about the rotation axis that passes through its centre. Optionally, the second rotary support apparatus further comprises a fixed gantry with a central bore operable to receive the rotatable gantry, wherein the rotatable gantry is mounted within the central bore of the fixed gantry and is configured to rotate with respect to the fixed gantry. Optionally, in some embodiments, the rotatable gantry is a drum gantry and the radiation shield is fixed inside the drum. Alternatively, in other embodiments, the radiation shield is fixed to an arm of the rotatable gantry extending outward from the gantry in an axial direction generally parallel to the radiation axis.

In some embodiments, the second rotary support apparatus comprises two concentric ring gantries with concentric central bores centred on the rotation axis. Opposite ends of the radiation shield are fixed to each of the ring gantries, such that the shield is positioned and fixed between the two gantries. The ring gantries are configured to rotate about the rotation axis to cause the radiation shield to rotate about the rotation axis.

In some embodiments, the second rotary support apparatus comprises one or more curved guides, and the radiation shield is slidably mounted to the one or more curved guides to travel along the guides. In some embodiments, each of the one or more curved guides are circular rings centred on the rotation axis. In other embodiments, each of the one or more curved guides form a semicircle centred on the rotation axis. In yet other embodiments each of the one or more curved guides form an arc of a circle centred on the rotation axis. In some embodiments, the radiotherapy system may comprise a fixed radiation shield extending between the opposite ends of the one or more curved guides.

In some embodiments, the radiotherapy system further comprises a second shield apparatus slidably mounted to the one or more curved guides to travel along the guides. In some embodiments, the first shield apparatus is slidably mounted on a first portion of the one or more curved guides, and the second shield apparatus is slidably mounted on a second portion of the one or more guides. In some embodiments, the position of the second shield apparatus on the second portion of the one or more guides is a reflection of the position of the first shield apparatus on the first portion, wherein the reflection is defined by a line of symmetry passing between the first and second portions of the guides and through the rotation axis.

In another aspect, there is disclosed a method of controlling the rotation of a radiation shield in a radiotherapy system. The method comprises rotating a radiation beam source about a rotation axis, wherein the radiation beam source is mounted on a first rotary support apparatus and is configured to emit a radiation beam. The method further comprises rotating a radiation shield about the rotation axis, wherein the radiation beam source is mounted on a second rotary support apparatus separate from the first rotary support apparatus and wherein rotation of the radiation shield is independent of the rotation of the radiation beam source.

In some embodiments, the method further comprises rotation the radiation shield about the second axis to maintain the radiation shield in the path of the radiation beam emitted by the radiation beam source.

BRIEF DESCRIPTION OF THE DRAWINGS

Specific embodiments are described below by way of example only and with reference to the accompanying drawings in which.

DETAILED DESCRIPTION OF THE DRAWINGS

The Figures and the description thereof illustrate specific embodiments of the present disclosure, which the skilled person will understand are non-limiting and are by way of example only.

Figure 1A:
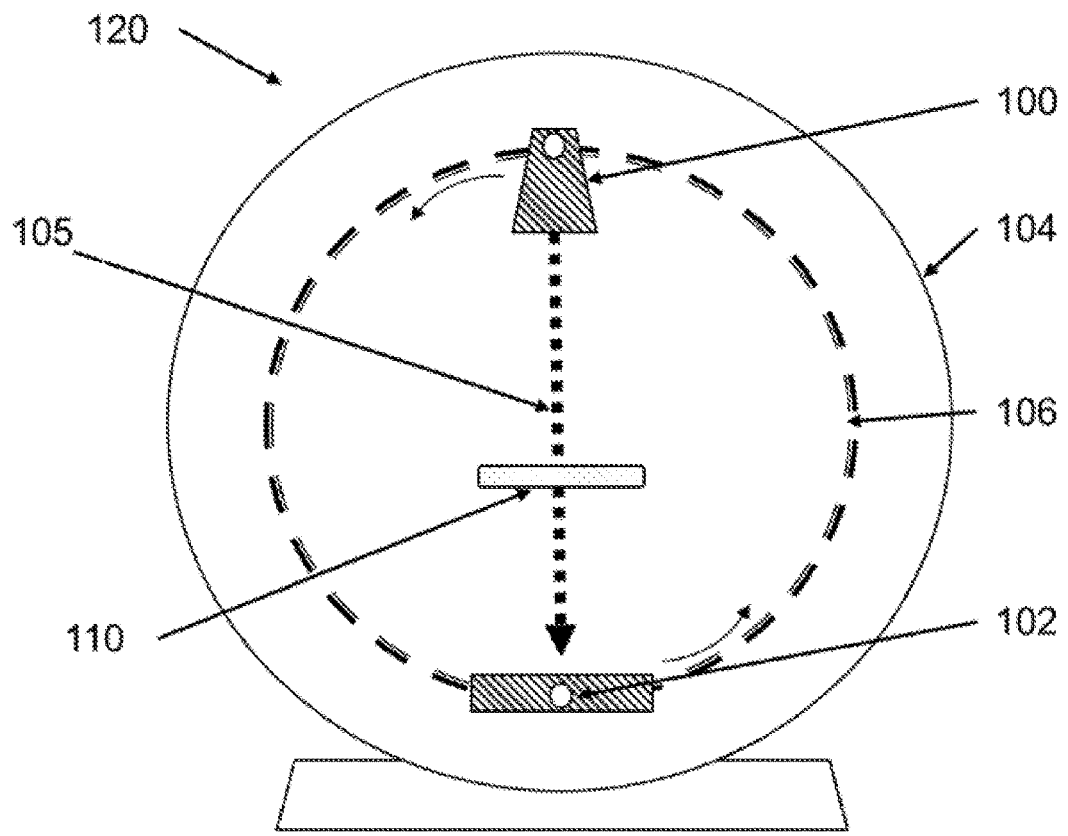
FIGS. 1a and 1b depict views of a radiotherapy device according to the prior art.
Figure 1B:
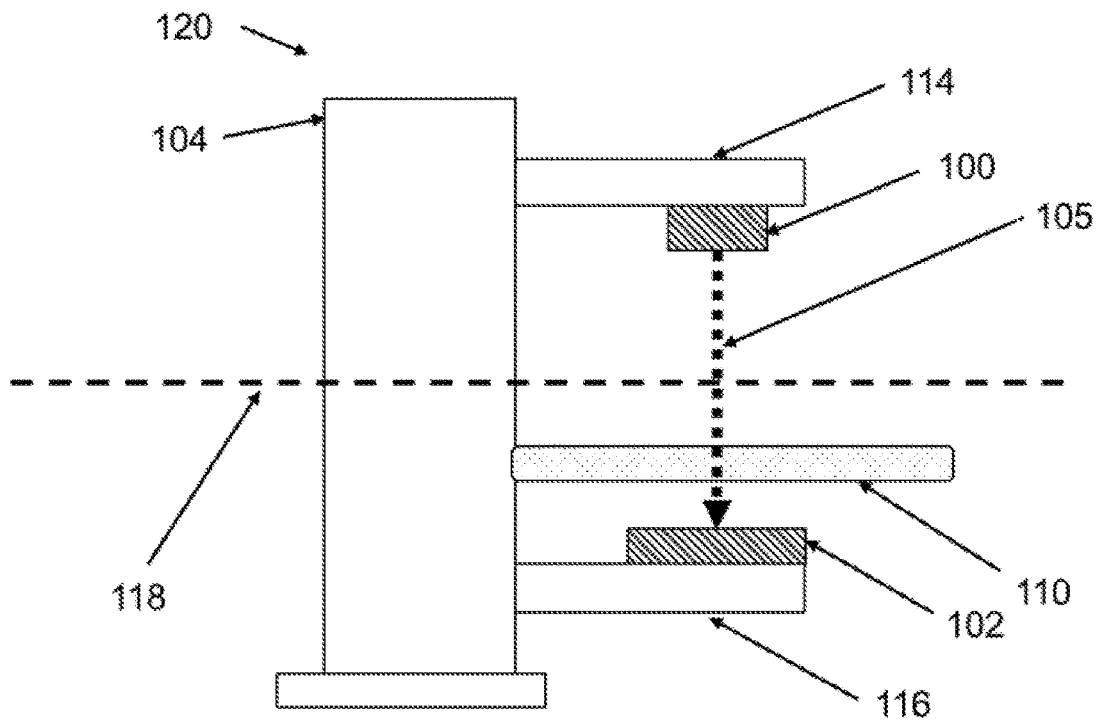

An example prior art radiotherapy device is shown in FIGS. 1a, and 1b. The figures show a cross-section through a radiotherapy device 120 comprising a radiation source 100 and a detector 102 attached to a gantry 104. The gantry comprises a circular support track 106. Dashed Arrow 105 indicates the direction of a radiation beam emitted from the radiation source 100. The radiation beam source 100 and the radiation shield are mounted on the gantry such that they are diametrically opposed to one another. The figures also show a patient support surface 110 suitable for supporting a patient (not shown) during radiotherapy treatment.

As radiation is delivered to a patient, for example according to a treatment plan, the radiation beam source 100 and the detector 102 rotate together around the circular support track 106, since both the source 100 and detector 102 are mounted to the gantry 104 which rotates around the circular support track. The source 100 and detector 102 are therefore always arranged 180° from one another as the gantry rotates. The rotation of the gantry around the circular support track is defined by a rotation axis (not shown in FIG. 1a) which passes through the centre of the gantry.

The radiation beam source 100 directs a radiation beam toward a patient lying on the patient support surface 110 from various angles around the patient in order to spread out the radiation dose received by heathy tissue to a larger region of healthy tissue while building up a prescribed dose of radiation at a target region. In FIGS. 1a and 1b, the radiation beam source 100 is at the top of the circular support track 106 and the detector 102 is diametrically opposed at the bottom of the circular support track 106.

FIG. 1b depicts a further view of an example prior art radiotherapy device. While FIG. 1a may depict a radiotherapy device 120 from a longitudinal end of the radiotherapy device 120, FIG. 1b may depict the radiotherapy device 120 from a lateral side of the radiotherapy device 120. In other words, FIG. 1b may depict a side profile of the radiotherapy device 120. From this view, it can be seen that the radiation beam source 100 is disposed on a support arm 114, which may connect the radiation beam source 100 to the gantry 104. The detector 102 is also disposed on a support arm 116, which may connect the beam stopper to the gantry 104. In this view, the rotation axis about which the gantry rotates is indicated by dashed line 118. The rotation axis passes through the centre of the gantry 104.

Figure 1C:
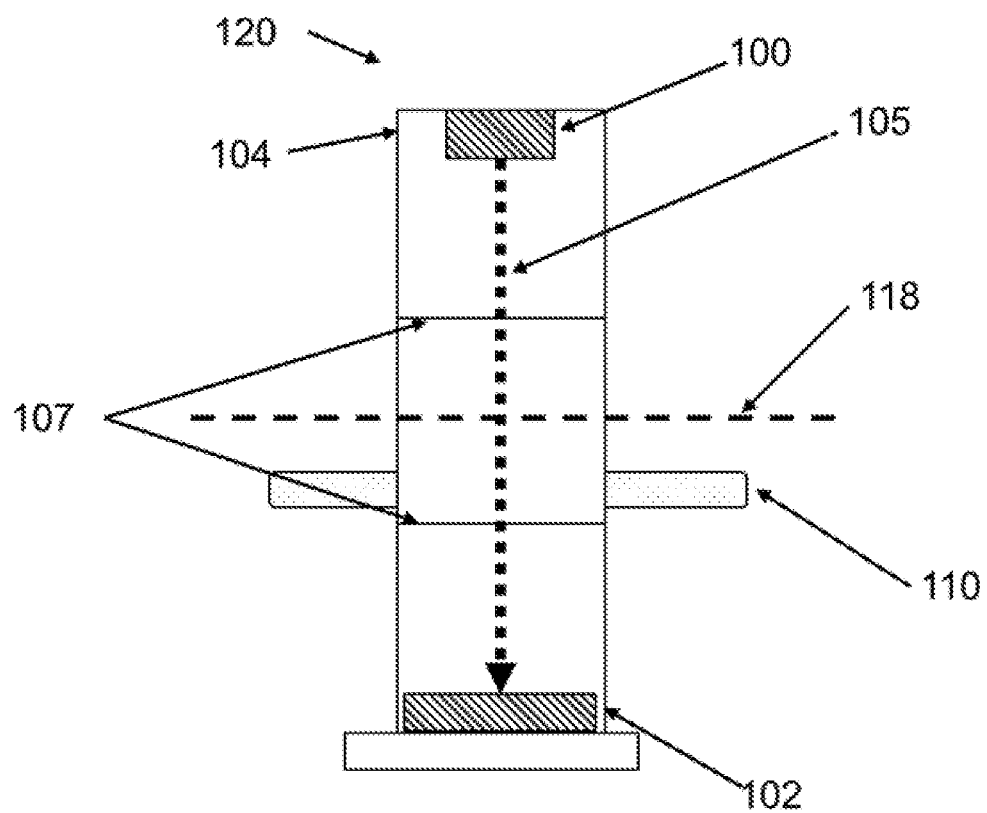
FIG. 1c illustrates another radiotherapy device according to the prior art.

FIG. 1c illustrates another example of a prior art radiotherapy device. This figure depicts a lateral view of the device similar to the view depicted in FIG. 1b. In this example, the gantry 104 has a central bore 107 configured to receive a patient support table 110 therein. The radiation source 100 and detector 102 are mounted to the gantry within the plane of the gantry itself such that the radiation beam is emitted within the plane of the gantry. In this example, the ionising radiation is delivered to an isocentre within the plane of rotation of the gantry. As with the examples illustrated in FIGS. 1a and 1b, the radiation source 100 and detector 102 are mounted to the rotating gantry 104.

Radiotherapy systems such as those depicted in FIGS. 1a-1c may optionally additionally comprise a shielding system. It is beneficial to provide a shielding system that attenuates the radiation beam that exits the patient in order to protect personnel and other equipment from gamma ray or X-ray radiation produced by the radiation source 100.

An issue with known radiation shielding systems is that the radiation shield typically needs to have a sufficient depth in order to sufficiently attenuate the radiation beam. Known radiation shielding material typically requires a heavy metal or heavy metal alloy including a heavy metal such as tungsten or lead, which results in a very heavy radiation shield. It is therefore problematic to fix such a heavy radiation shield to the gantry such that the radiation shield is always diametrically opposed to the radiation beam source, since this can cause issues with on-gantry weight distribution. Additionally, increasing the on-gantry weight requires a more structurally robust and therefore more expensive gantry to support the weight of the on-gantry components (the radiation source, detector, and radiation shield). It is therefore desirable to provide a radiotherapy system with a rotating radiation beam source and radiation shield that has an improved load distribution.

Figure 2A:
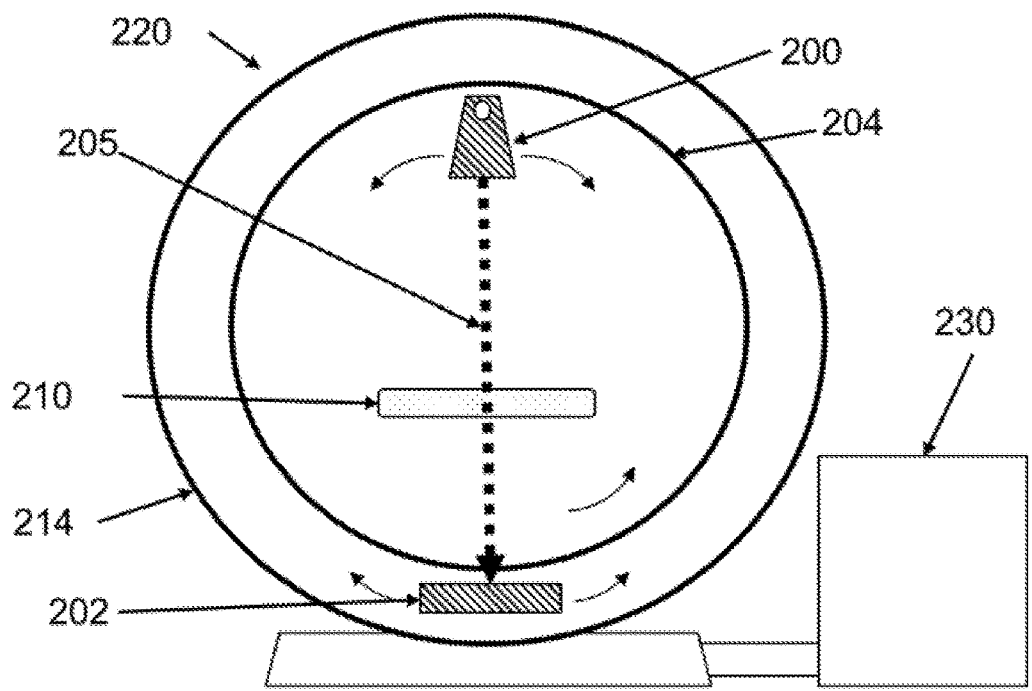
FIGS. 2a and 2b illustrate a radiotherapy system according to a first embodiment of the present disclosure.
Figure 2B:
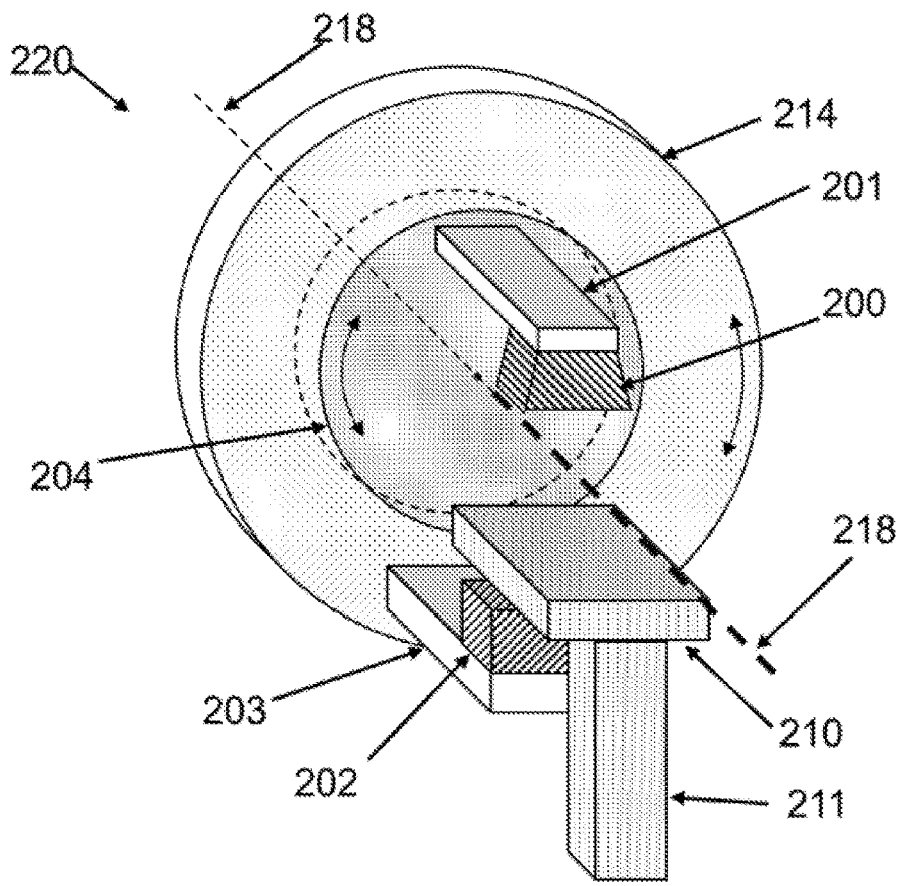

FIGS. 2a and 2b depict a radiotherapy system 220 according to some embodiments of the present disclosure. The system is suitable for and configured to direct radiation toward a patient, for example according to a radiotherapy treatment plan. In the illustrated example, the radiotherapy system comprises a first rotary support apparatus 204, a second rotary support apparatus 214, a radiation beam source 200, a radiation shield 202, and a patient support surface 210.

The radiation beam source 200 is configured to provide a beam of therapeutic radiation to a patient. The radiation source 200 may be any of a number of different types of radiation sources known to the skilled person, for example a kilovoltage therapy X-ray unit or a linear accelerator (LINAC).

The radiotherapy system 220 may also further comprise a radiation detector (not shown). The radiation detector may be any suitable radiation detector and may comprise imaging means, i.e. imaging apparatus or an imaging device, to allow imaging of the patient. For example, the imaging device may comprise a portal imaging detector. The detector allows radiotherapists to plan image guided radiotherapy treatments according to known techniques.

The radiotherapy system 220 further comprises a first rotary support apparatus 204 configured to rotate about a rotation axis (indicated by dashed line 218 in FIG. 2b) passing through the centre of the first rotary support apparatus. In the illustrated example, the radiation beam source 200 is mounted to the first rotary support apparatus 204 such that the radiation beam source 200 is configured to rotate about the rotation axis as the first rotary support apparatus rotates. In other words, the radiation beam source 200 is configured to rotate about the rotation axis such that the radiation beam source 200 traverses a curved path centred on the rotation axis. In some examples, the first rotary support apparatus 204 is configured to rotate through 360° and thus the radiation beam source 200 is configured to traverse a circular path centred on the rotation axis as the first rotary support apparatus 204 rotates. In other examples, the first rotary support apparatus 204 is configured to rotate through an amount less than 360°, optionally 180°, and so the radiation beam source 200 is configured to traverse an arcuate path, optionally a semi-circular path, centred on the rotation axis.

In some embodiments, the first rotary support apparatus 204 does not itself rotate about the rotation axis but is configured to cause a radiation beam source 200 mounted to the first rotary support apparatus to rotate about the rotation axis. For example, the first rotary support apparatus may comprise static guides, such as circular or otherwise curved guides, to which the radiation beam source is slidably mounted. The radiation beam source may be slidably mounted such that it can travel along the guides. The first rotary support apparatus may comprise any suitable drive system configured to cause the radiation beam source to travel along the curved guides. It would be appreciated that in this example, and other similar examples, the first rotary support apparatus does not itself rotate (i.e, the curved guides are static and do not themselves rotate), but does cause rotation of the radiation beam source (for example, by the drive system causing the radiation beam source to travel along the guides).

In some embodiments of the present disclosure, the radiotherapy system 220 does not include the radiation beam source 200.

The first rotary support apparatus 204 may be any apparatus suitable for supporting a radiation beam source that is configured to cause the radiation beam source 200 to rotate about a rotation axis passing through the centre of the apparatus 204. For example, the first rotary support apparatus may be a rotatable gantry such as a ring gantry, drum gantry or C-arm gantry, or any type of gantry suitable for supporting a radiation beam source that would be apparent to the skilled person. In the specific illustrated example of the radiotherapy device according to some embodiments of the present disclosure, the first rotary support apparatus is a ring gantry configured to rotate about the rotation axis that passes through the centre of the ring.

The radiotherapy system 220 further comprises a radiation shield 202 mounted a second rotary support apparatus 214. In some embodiments, the second rotary support apparatus 214 is configured to rotate about the rotation axis passing through the centre of the second rotary support apparatus, thus causing the radiation shield 202 to rotate about the rotation axis. In other embodiments, the second rotary support apparatus 214 does not itself rotate about the rotation axis, but is configured to cause the radiation shield 202 to rotate about the rotation axis. In other words, the radiation shield 202 is configured to rotate about the rotation axis such that the radiation shield traverses a curved path centred on the rotation axis. In some examples, the second rotary support apparatus 214 is configured to cause the radiation shield 202 to rotate through 360° and thus the radiation shield 202 is configured to traverse a circular path centred on the rotation axis as the second rotary support apparatus 214 rotates. In other examples, the second rotary support apparatus 214 is configured to cause the radiation shield 202 to rotate through an amount less than 360°, optionally 180°, and so the radiation shield 202 is configured to traverse an arcuate path, optionally a semi-circular path, centred on the rotation axis.

The radiation shield 202 may be any suitable radiation shield that is suitable for attenuating a beam of radiation, such as a beam of radiation emitted from a radiation beam source. In examples, the radiation shield is suitable to attenuate a beam of radiation such that none of the radiation beam passes through the radiation shield. In other words, the radiation shield attenuates 100% of the beam. In other examples, the radiation shield may be configured to attenuate less than 100% of a beam of radiation. In other words, the radiation shield may instead reduce the intensity of the radiation beam but still allow some radiation to pass through the radiation shield, for example to be received by a radiation detector behind the radiation shield.

The radiation shield is typically made of a heavy metal such as tungsten or lead, or an alloy combining heavy metals and other suitable materials apparent to the skilled person. The radiation shield may otherwise be made of any other suitable material capable of attenuating a radiation beam that would be apparent to the skilled person.

Similar to the first rotary support apparatus 204, the second rotary support apparatus 214 may be any apparatus suitable for supporting a radiation shield that is configured to rotate about the rotation axis passing through the centre of the apparatus 214, or that is configured to cause the radiation shield 202 to rotate about the rotation axis. For example, the second rotary support apparatus may be a rotatable gantry such as a ring gantry, drum gantry or C-arm gantry, or any type of gantry suitable for supporting a radiation shield that would be apparent to the skilled person. In the specific illustrated example of the radiotherapy device according to some embodiments of the present disclosure, the second rotary support apparatus 414 is a ring gantry configured to rotate about the rotation axis that passes through the centre of the ring.

The radiotherapy apparatus 220 optionally further comprises a patient support surface 210. The support surface is suitable for receiving a patient thereon and is suitable to position the patient for radiotherapy treatment, for example according to a treatment plan. The patient support surface 210 may be moved longitudinally relative to the gantry 104, for example to aid positioning of a patient lying on the support surface. In other words, the support surface 210 may be configured to move in an axial direction generally parallel to the first rotation axis to position the patient during treatment. The patient support surface may further be configured to move laterally, generally orthogonal to the rotation axis, or move in any other manner in order to position the patient for treatment. In some examples, the radiotherapy device may comprise a central bore suitable for receiving the patient support surface therein. In other words, the patient support surface 210 may be moved in a longitudinal direction to position a patient lying on the patient support surface within a central bore of the radiotherapy device. FIG. 2b illustrates a perspective view of the radiotherapy device 220. In this view, it can be seen that the patient support surface comprises a support stand 211 which may aid the positioning of the support surface.

In embodiments of the present disclosure, the patient support table may be included as a part of the radiotherapy device according to embodiments, or may instead be a separate component not included as part of the radiotherapy device. The skilled person would understand that the advantages enabled by the present disclosure do rely on the presence of the patient support surface, and as such the patient support surface 210 is an optional feature.

As discussed above, in the specific illustrated example of the radiotherapy device in FIGS. 2a and 2b, the first and second rotary support apparatuses are ring gantries. As can be seen in the perspective view of the radiotherapy device provided in FIG. 2b, the rang gantries are coplanar. In other words, the first and second support apparatuses 204 and 214 are disposed in the same rotation plane. In the specific illustrated example it can be seen that the first rotary support apparatus 204 is disposed inside the second rotary support apparatus 214. In other words, the first rotary support apparatus 204 rotates within the second rotary support apparatus 214 about the rotation axis, and the second rotary support apparatus 214 rotates around the first rotary support apparatus 214 and about the rotation axis. It may be said that the first rotary support apparatus is therefore an 'inner' rotary support apparatus, and the second rotary support apparatus is an 'outer' rotary support apparatus. In some embodiments wherein the first and second rotary support apparatuses are coplanar, the second rotary support apparatus may instead be disposed within the first rotary support apparatus. In other words the second rotary support apparatus may be the 'inner' rotary apparatus, and the first rotary support apparatus may be the 'outer' rotary support apparatus.

In some embodiments wherein the first and second rotary support apparatuses are coplanar, the 'inner' rotary support apparatus may comprise a central bore (not shown) suitable for receiving a patient lying on a patient support table 210.

As can be seen from the specific embodiment illustrated in FIG. 2b, the radiation beam source 200 is mounted to the first rotary support apparatus 204 via a first support arm 201 connecting the radiation beam source to the first rotary support apparatus 204. Similarly, the radiation shield 202 is mounted to the second rotary support apparatus 214 via a second support arm 203. In the illustrated embodiment, the radiation beam source and radiation shield are therefore disposed longitudinally away from the first and second rotary support apparatus.

In other embodiments, the radiation beam source 200 and radiation shield 202 may instead be mounted to the first and second rotary support apparatuses respectively such that they are positioned within the rotation plane of the respective support apparatuses. It would be apparent to the skilled person that the radiation shield 202 can be mounted to the second rotary support apparatus 214 in any manner that causes the radiation shield to be able to rotate about the rotation axis, and that the first rotary support apparatus 204 can be configured in any suitable manner for supporting the radiation beam source 200.

In some embodiments, the rotation of the radiation shield 202 is synchronised with rotation of the radiation beam source 200. In other words, the first and second rotary support apparatuses are coupled that the radiation shield and radiation source are configured to rotate at the same time. It may be considered that the radiation shield maintains a fixed position relative to the radiation beam source as the radiation beam source rotates, or vice versa. The fixed position may be such that the radiation shield is always in the path of a radiation beam emitted by the radiation beam source as the radiation beam source rotates about the rotation axis. As an example, in some embodiments, the rotation of the radiation shield 202 is synchronised with the rotation of the radiation beam source 200 such that the radiation shield is always positioned to be diametrically opposed to the radiation beam source as the radiation beam source rotates about the rotation axis.

In some embodiments, the rotation of the radiation beam source is synchronised with the rotation of the radiation shield by means of a mechanical rotary coupling system. In other words, the first and second rotary support apparatuses may be mechanically coupled by means of an arrangement of gears or pulleys, or any other suitable system that couples rotation of the radiation beam source with rotation of the radiation shield. In some embodiments, the radiotherapy system may comprise a rotary drive system that directly drives rotation of the radiation beam source about the rotation axis. The rotation of the radiation beam source may then in turn drive rotation of the radiation shield via the mechanical coupling. Alternatively, the rotary drive system may directly drive rotation of the radiation shield which then in turn drives the rotation of the radiation beam source via the mechanical coupling. In other embodiments, a single rotary drive system may simultaneously directly drive the rotation of each of the radiation beam source and radiation shield such that their respective rotations are synchronised.

In alternative embodiments, the rotation of the radiation beam source is synchronised with the rotation of the radiation shield by means of an electrical coupling system. FIG. 2a depicts a control system 230 that is configured to control the rotation of the radiation shield and/or the rotation of the radiation beam source, such that the respective rotations are synchronised. In some examples, the radiotherapy system may comprise separate rotary drive systems for each of the radiation beam source and radiation shield, and the control system may control each of the drive systems in order to synchronise the rotation of the radiation beam source and radiation shield.

In alternative embodiments, the rotation of the radiation beam source and radiation shield may not be synchronised but instead may be independent of one another. In other words, the radiation shield may be configured to be able to rotate about the rotation axis independently of the rotation of the radiation beam source Embodiments of the present disclosure provide a separate support (the second rotary support apparatus) for supporting the weight of the radiation shield. This enables the on-gantry weight of the first rotary support apparatus (that supports the radiation source) to be minimized and improves weight distribution across the whole radiotherapy system. Embodiments of the present disclosure further comprise a control system or other coupling system that causes the rotation of the radiation shield and radiation beam source to be synchronised. Thus, even though each of these components are mounted to separate rotary apparatuses, it is still possible to ensure that the radiation shield is, for example, always diametrically opposed to the radiation beam source in order to effectively attenuate a radiation beam.

In addition to the above-described advantages, embodiments of the present disclosure also provide a more adaptable radiotherapy system. Since the rotary support apparatus for the radiation shield is separate to the rotary support apparatus for the radiation beam source, each apparatus can be provided as separate, modular components of the system that may be attachable and detachable. This can facilitate simplified transportation, installation, repair and maintenance of the radiotherapy system.

Figure 3A:
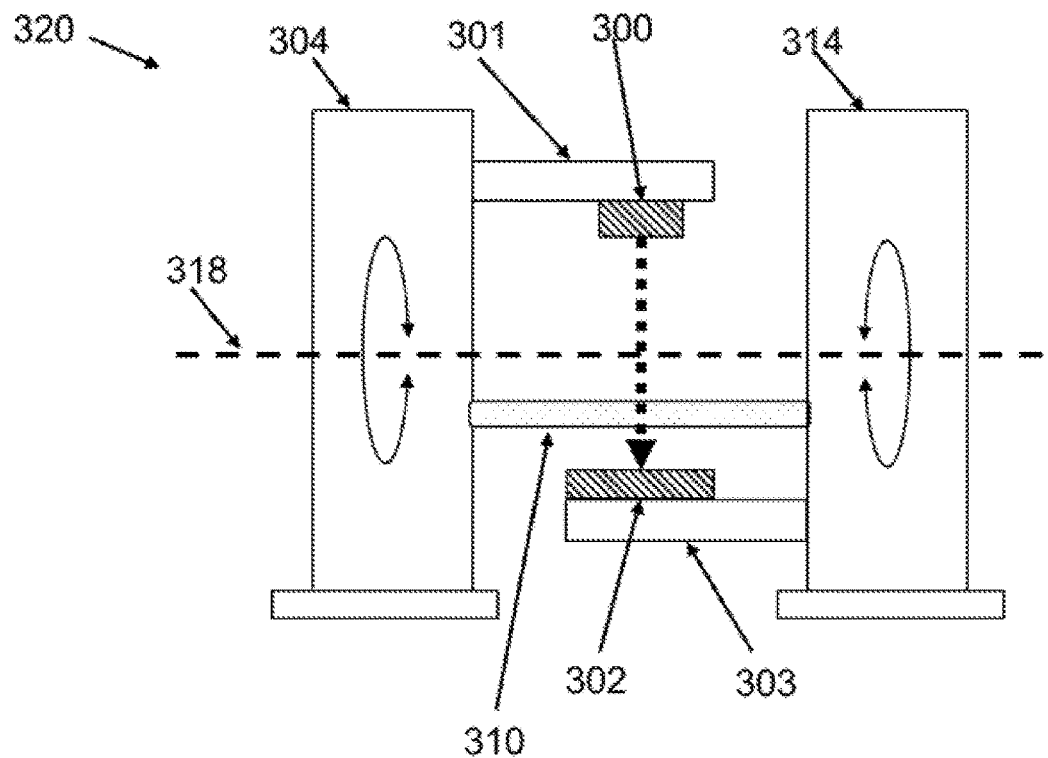
FIG. 3a illustrates a radiotherapy system according to a second embodiment of the present disclosure.

FIG. 3a illustrates a radiotherapy system according to a second embodiment of the present disclosure. As with the embodiment depicted in FIGS. 2a and 2b, the radiotherapy system 320 comprises a first rotary support apparatus 304 comprising a first support arm 301. In this embodiment, a radiation beam source 300 is mounted to the first support arm 301 and the first rotary support apparatus 304 is configured to cause the radiation beam source 300 to rotate about a rotation axis (indicated by dashed line 318). The radiotherapy system further comprises a patient support table 310, a second rotary support apparatus 314 and a radiation shield 302 connected to the second rotary support apparatus via a second support arm 303. The second rotary support apparatus is configured to cause the radiation shield to rotate about the rotation axis (also indicated by dashed line 318). The radiotherapy system may further comprise a control system (not shown) similar to control system 230 in FIG. 2a, which may be configured to control the rotation of the radiation shield and/or the radiation beam source such that they are synchronised with one another, for example to ensure that the radiation shield 302 is always diametrically opposed to the radiation beam source. Alternatively, the radiotherapy system may comprise any suitable mechanical coupling apparatus as described above that couples rotation of the radiation beam source with rotation of the radiation shield.

As can be seen from FIG. 3a, the first and second rotary support apparatus 304 and 314 are not coplanar (unlike the embodiment illustrated in FIG. 2b) but instead the first and second rotary support apparatuses are positioned separately along the rotation axis 318. In other words, the first and second rotary support apparatuses are separated by a distance in a longitudinal direction along the common rotation axis 318. In this embodiment, the second rotary support apparatus 314 is a rotatable gantry such as a ring gantry, drum gantry, or a C-arm gantry that is configured to rotate about the rotation axis 318. Therefore, rotation of the radiation shield about the rotation axis 318 is caused by the rotation of the second rotary support apparatus itself about the rotation axis 318, to which the radiation shield is connected via second support arm 303. In other embodiments, rotation of the radiation shield about the rotation axis may be caused by any suitable rotary support apparatus that is suitable to cause rotation of the radiation shield about the rotation axis.

Figure 3B:
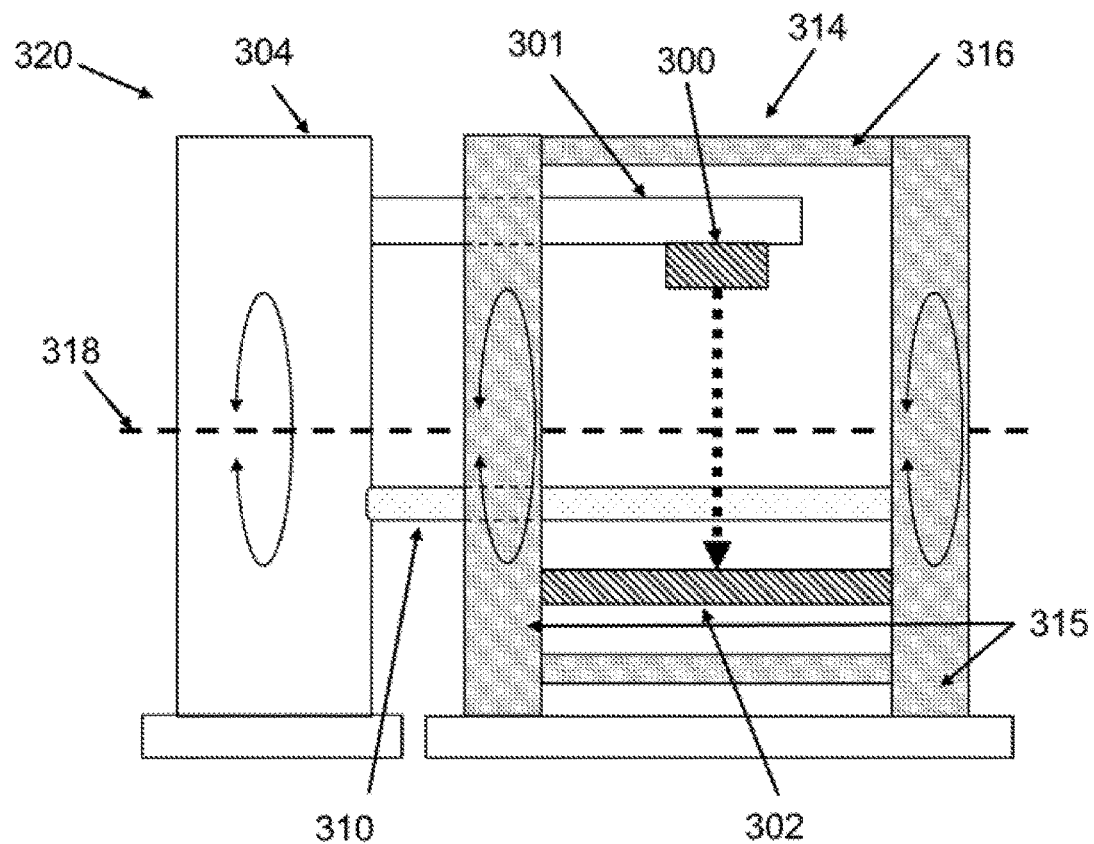
FIG. 3b illustrates a radiotherapy system according to a third embodiment of the present disclosure.

FIG. 3b illustrates a further embodiment of a radiotherapy system according to some examples of the present disclosure, where like reference numerals as used with respect to FIG. 3a have been used to depict like components. In the embodiment depicted in FIG. 3b, the second rotary support apparatus 314 comprises two concentric rotatable gantries 315 with concentric central bores (not shown) operable to receive a patient lying on a patient support table 310 therein. The central bore of one or both gantries may optionally also be operable to receive a radiation beam source 300 mounted to a first support arm 301 of a first rotary support apparatus 304 configured to cause the radiation beam source to also rotate about axis 318. Alternatively, the radiation beam source 300 and support arm 301 may be positioned outside of the rotatable gantries 315 such that the radiation beam source 300 rotates around the outside of the gantries.

The radiation shield 302 is positioned in between the two rotatable gantries 315 and is connected at its end to each of the rotatable gantries. In other words, opposite ends of the radiation shield 302 are each fixed to one of the rotation gantries 315 such that the radiation shield is fixed between the two rotating gantries. The rotating gantries may additionally be connected by one or more supporting beams 316 to provide structural support.

The rotating gantries 315 are configured to rotate about the rotation axis 318 thus causing the radiation shield to rotate about the rotation axis. As discussed with reference to FIGS. 2a and 2b, the rotation of the rotating gantries 315 and thus the radiation shield 302 may be synchronised with the rotation of the radiation beam source 300. As an example, the rotation of the rotating gantries may be synchronised with rotation of the radiation beam source such that that radiation shield is always diametrically opposed to the radiation beam source. For example, the radiotherapy system may further comprise a control system (not shown) similar to control system 230 in FIG. 2a, which may be configured to control the rotation of the radiation shield and/or the radiation beam source such that they are synchronised with one another, for example to ensure that the radiation shield 302 is always diametrically opposed to the radiation beam source. Alternatively, the radiotherapy system may comprise any suitable mechanical coupling apparatus as described above that couples rotation of the radiation beam source with rotation of the radiation shield.

Figure 4A:
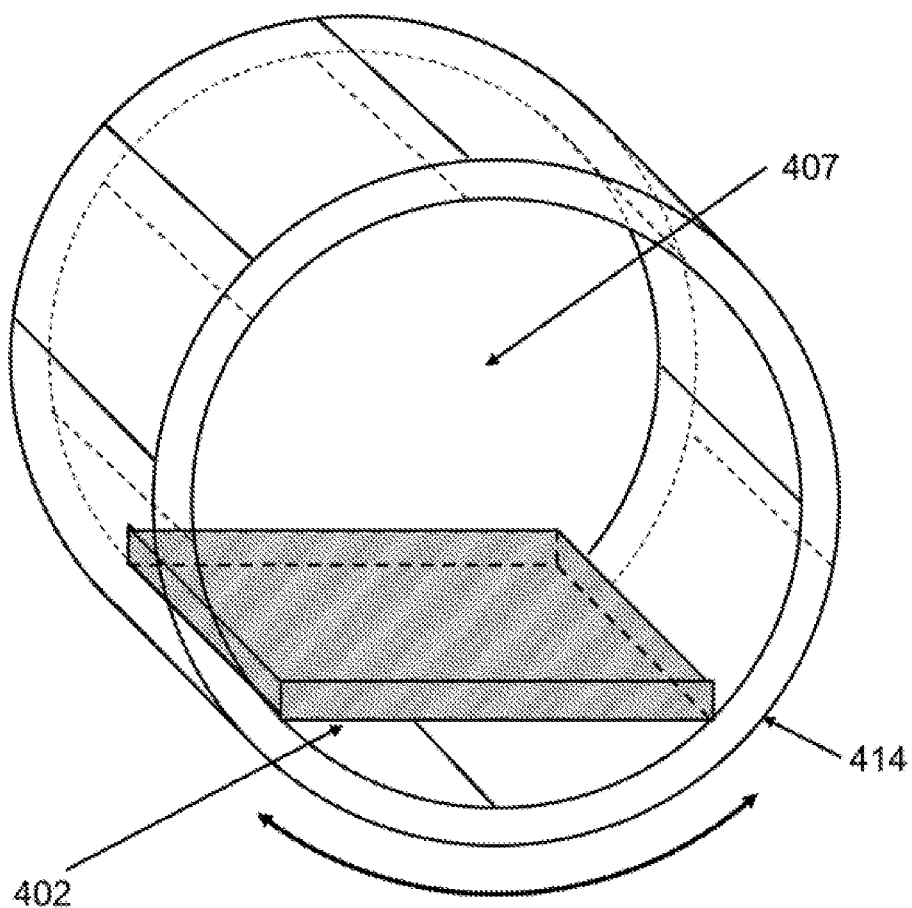
FIG. 4a illustrates a second rotary support apparatus for a radiation shield according to a fourth embodiment of the present disclosure.

With reference to FIG. 4a, a perspective view of a second rotary support apparatus 414 according to some embodiments of the present disclosure is depicted. The second rotary support apparatus 414 is suitable to be used as part of a radiotherapy system according to the present disclosure, wherein the radiotherapy system comprises a first rotary support apparatus for supporting a radiation beam source and causing the radiation beam source to rotate about a rotation axis, and further comprises a radiation shield mounted to the second rotary support apparatus, wherein the second rotary support apparatus configured to cause the radiation shield to rotate about the rotation axis.

The second rotary support apparatus 414 illustrated in FIG. 4a is a rotatable gantry configured to rotate about the rotation axis. The rotation axis passes through the centre of the rotatable gantry such that the apparatus 414 rotates about its own central axis. In more detail, in this specific embodiment, the second rotary support apparatus is a drum gantry with a central bore 407. The central bore is suitable for receiving a patient lying on a patient support table and the drum gantry 414 is configured to rotate about the patient and the patient support table. Optionally, the central bore may be suitable to receive a radiation beam source mounted on a support arm (not shown in this figure) such as the support arm described with reference to FIG. 2b, 3a or 3b. The gantry may therefore rotate about the radiation beam source and the support arm received in the central bore. Additionally, the radiation beam source may be configured to rotate about the first rotation axis within the drum gantry 414. As can be seen in FIG. 4a, a radiation shield 402 is fixed inside the drum gantry, optionally on one side of the drum gantry as illustrated, and is configured to rotate about the rotation axis as a result of the drum gantry rotating about the rotation axis. The rotation of the radiation shield 402 may be synchronised with the rotation of radiation beam source. As an example, the rotation of the drum gantry 414 may be synchronised with rotation of the radiation beam source such that that radiation shield 402 is always diametrically opposed to the radiation beam source. For example, the radiotherapy system may further comprise a control system (not shown) similar to control system 230 in FIG. 2a, which may be configured to control the rotation of the radiation shield and/or the radiation beam source such that they are synchronised with one another, for example to ensure that the radiation shield 302 is always diametrically opposed to the radiation beam source. Alternatively, the radiotherapy system may comprise any suitable mechanical coupling apparatus as described above that couples rotation of the radiation beam source with rotation of the radiation shield.

Figure 4B:
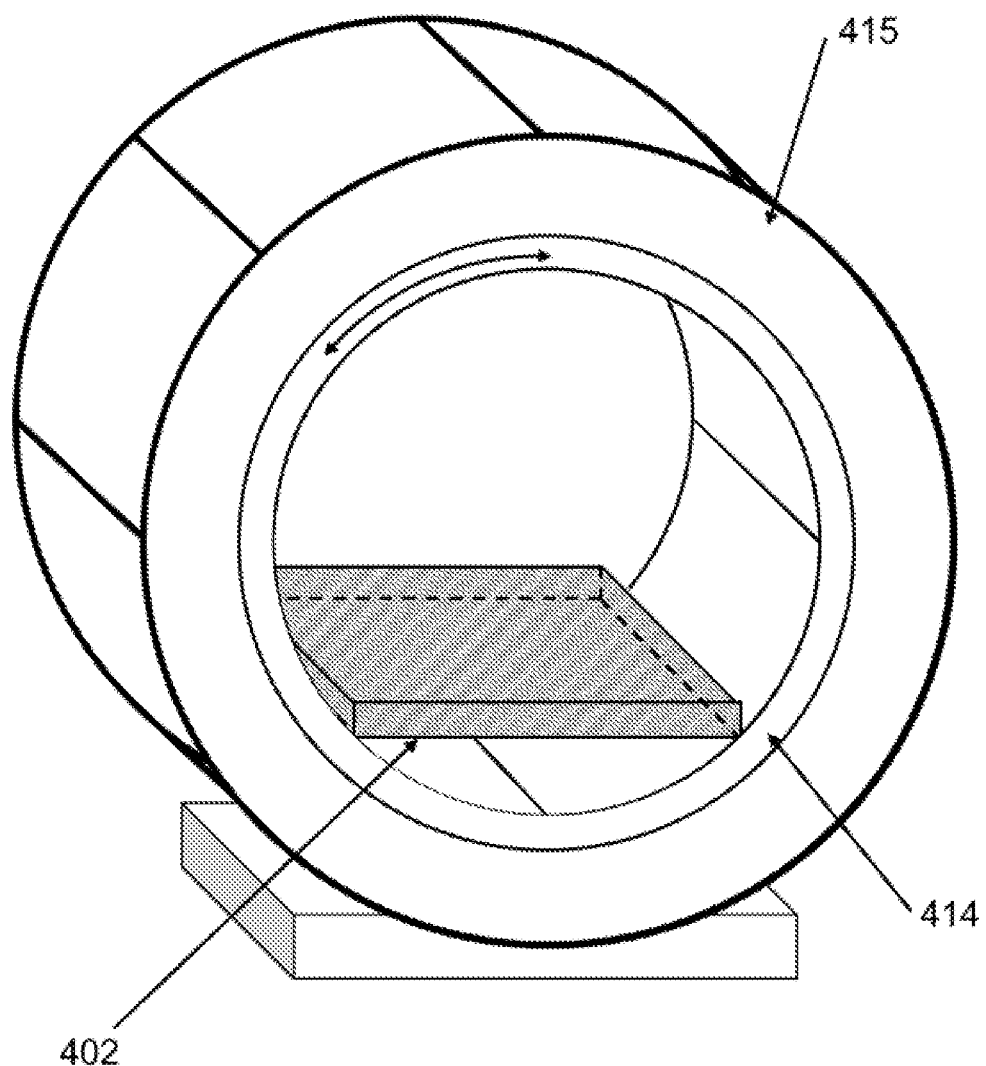
FIG. 4b illustrates the second rotary support apparatus of FIG. 4a received within a central bore of a fixed gantry according to a fifth embodiment of the present disclosure

FIG. 4b illustrates a perspective view of an embodiment of the present disclosure wherein the second rotary support apparatus 414 illustrated in FIG. 4a is received within a central bore of a fixed gantry 415. The second rotary support apparatus 414 is rotatably mounted within the central bore of the fixed gantry 415 such that the second rotary support apparatus is operable to rotate within the fixed gantry, and with respect to the fixed gantry, about the rotation axis.

Figure 5A:
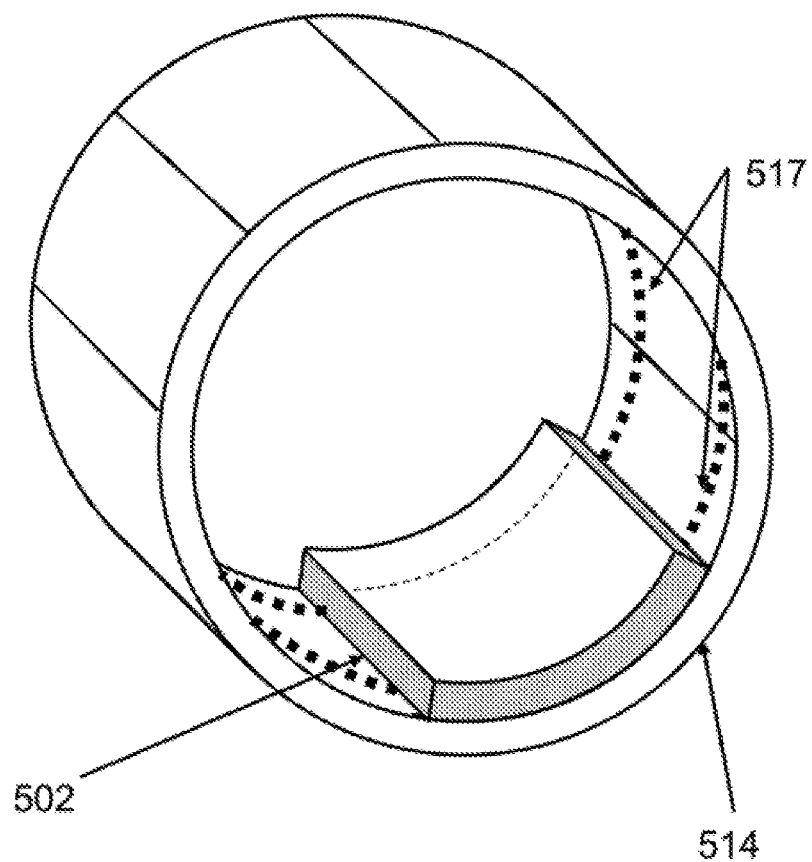
FIGS. 5a and 5b illustrates a second rotary support apparatus for a radiation shield according to a sixth embodiment of the present disclosure.

With reference to FIG. 5a, a perspective view of a second rotary support apparatus 514 according to some embodiments of the present disclosure is shown. The second rotary support apparatus 514 is suitable to be used as part of a radiotherapy system according to the present disclosure, wherein the radiotherapy system comprises a first rotary support apparatus for supporting a radiation beam source and causing the radiation beam source to rotate about a rotation axis, and further comprises a radiation shield mounted to the second rotary support apparatus, wherein the second rotary support apparatus configured to cause the radiation shield to rotate about the rotation axis.

In the embodiment illustrated in FIG. 5a, the second rotary support apparatus 514 comprises curved guides 517 to which the radiation shield 502 is slidably mounted. In other words, the radiation shield is able to travel along the curved guides. In the illustrated example, the second rotary support apparatus 514 comprises two curved guides 517 (depicted by the dashed black lines), however embodiments may include any number of one or more curved guides. The curved guides may be rails, tracks, grooves or any other suitable guide apparent to the skilled person that is suitable for slidably mounting a radiation shield such that the radiation shield is able to travel along the curved guides.

In the specific illustrated embodiment of FIG. 5a, the curved guides are circular rings centred on the rotation axis. The radiation shield is operable to travel along the curved guides and thus follow a circular path centred on the rotation axis, thus providing the rotation of the radiation shield about the first radiation axis.

In other embodiments, the curved guides may not form a full circle for the radiation shield to travel around but may instead be semi-circular. In other words, the curved guides may form a semi-circle, or half of a circle, that is centred on the rotation axis. In these embodiments, the radiation shield is operable to travel along the semicircle and thus rotate through 180° about the rotation axis.

In further embodiments, the curved guides may form an arc of a circle centred on the radiation axis, wherein the arc defines any proportion of the full circumference of the circle. As an example, the arc may form a quarter of a circle and thus the ends of the arcs subtend an angle of 90° using the centre of the circle (the rotation axis) as the vertex. In this example, the radiation shield is able to travel along the curved guides such that it can rotate through 90° about the rotation axis. In another example, the arc may form a portion of a circle that is greater than a semicircle but not a full circle. In this example, the ends of the arcs subtend an angle greater than 180° and less than 360° using the centre of the circle as the vertex. Thus the radiation shield in this example is able to travel along the curved guides such that it can rotate through more than 180° but less than 360° about the rotation axis.

In embodiments wherein the curved guides form an arc of a circle, the system may further comprise a fixed radiation shield positioned between opposite ends of the arc. As an example, the curved guides may be semi circular allowing the radiation shield to rotate about the rotation axis through 180°. The system may further comprise a stationary radiation shield that is positioned between the opposite ends of the semi-circular curved guides in order to provide shielding through 360°. The stationary radiation shield may also be semi-circular and thus follow the curvature of the guides, or may otherwise be flat or any other suitable shape. The fixed radiation shield may be fixed to a base of a radiotherapy system and thus provide radiation shielding at the base of the radiotherapy system.

Figure 5B:
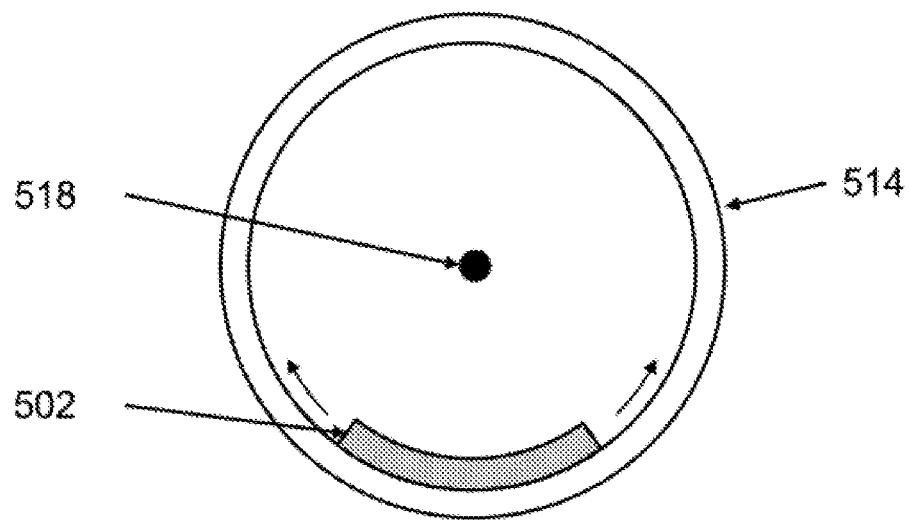

FIG. 5b illustrates a front view of the second rotary support apparatus and radiation shield of FIG. 5a. Circle 518 indicates the centre of the circle formed by the curved guides 517 (not shown in this view) and indicates the position of the rotation axis passing through the second rotary support apparatus. The radiation shield 502 travels along the curved guides (in the direction of the depicted curved arrows) such that the shield rotates about the rotation axis.

Figure 5C:
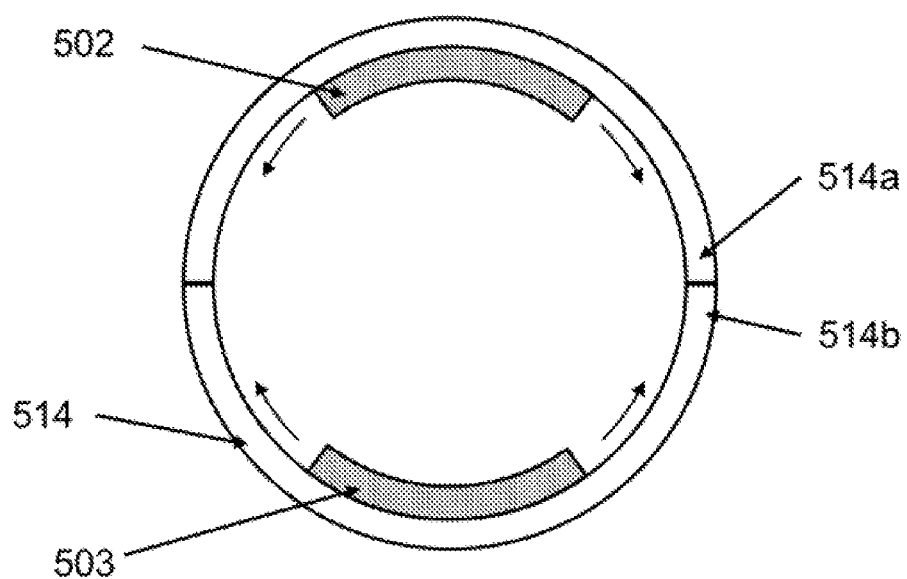
FIG. 5c illustrates a second rotary support apparatus for a radiation shield according to a seventh embodiment of the present disclosure.

FIG. 5c illustrates a further embodiment of a second rotary support apparatus 514 comprising curved guides to which the radiation shield is slidably mounted. In this embodiment, a second radiation shield 503, in addition to radiation shield 502, is also slidably mounted to the curved guides such that it can travel along the curved guides and rotate about the rotation axis in a similar manner to radiation shield 502. In other words, the second rotary support apparatus comprises a first radiation shield 502 and a second radiation shield 503 both slidably mounted to the curved guides, in order to travel along the curved guides and thus rotate about the rotation axis.

In the specific embodiment illustrated in FIG. 5c, the second rotary support apparatus 514 is comprised of a first portion 514a and a second portion 514b. The first radiation shield 502 is mounted to curved guides (not shown) of the first portion 514a and the second radiation shield is mounted to curved guides (not shown) of the second portion 514b. The curved guides of the respective first and second portions may be separate such that the first radiation shield can only travel along the curved guides of the first portion and the second radiation shield can only travel along the curved guides of the second portion. In other examples, the second rotary support apparatus may comprise one or more curved guides 517, wherein the first radiation shield 502 is mounted on a first portion 517a (not shown) of the one or more curved guides and the second radiation shield 503 is mounted on a second portion 517b (not shown) of the one or more curved guides. In some embodiments, the first and second portions of the curved guides are separate meaning that movement of the first radiation shield 502 along the first portion 517a of the curved guides does not interfere with movement of the second radiation shield 503 along the second portion 517b of the curved guides.

Figure 5D:
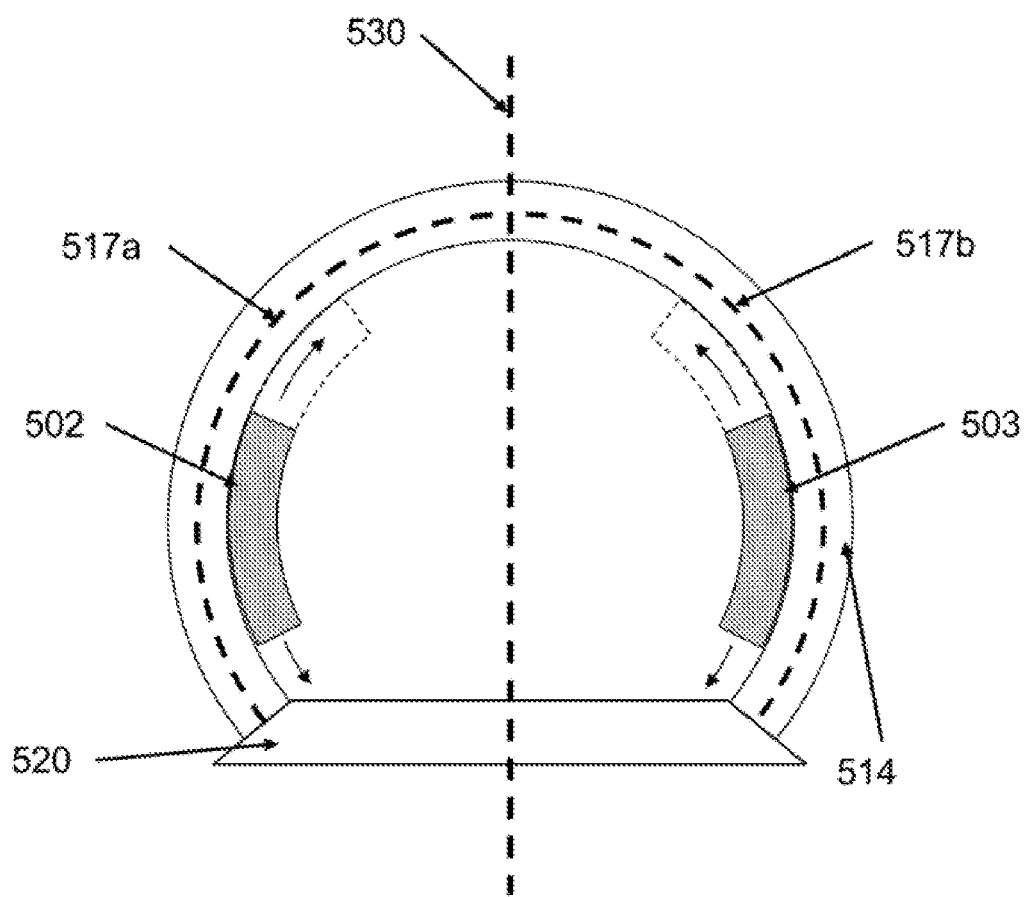
FIG. 5d illustrates a second rotary support apparatus for a radiation shield according to an eighth embodiment of the present disclosure.

FIG. 5d illustrates a specific embodiment of the second rotary support apparatus in which a first radiation shield 502 is slidably mounted to a first portion of one or more curved guides, and a second radiation shield is slidably mounted to a second portion of one or more curved guides. In this embodiment, movement of each of the radiation shields along their respective curved guides is interrelated or synchronised such that a position of the first radiation shield 502 on the first portion of the curved guide (indicated by dashed line 517a) is a reflection of the position of the second radiation shield 503 on the second portion of the curved guide (dashed line 517b), through the reflection line indicated at 530.

The reflection line 530 represents a plane of symmetry for the position of the first and second radiation shield on their respective curved guide portions. The rotation axis about which the radiation shield rotates lies within the plane of symmetry, and the plane passes between the first and second portions of the curved guides. Thus, as the first or second radiation shield moves along its respective curved guide portion, the opposite shield also moves in an identical manner such that the positions of the shields are a reflection of one another through the reflection plane.

In this specific illustrated embodiment the second rotary support apparatus and the curved guides form an arc of a circle. A base 520, optionally comprising a further stationary radiation shield, is positioned between the opposite ends of the apparatus 514. It would be apparent to the skilled person that the reflection of positions of the radiation shields as discussed above is equally applicable to embodiments wherein the curved guides form a full circle.

Features of the above disclosed embodiments can be combined in any suitable manner. The implementations disclosed herein have been described by way of example only, and the described implementations and arrangements are to be considered in all respects only as illustrative and not restrictive. It will be appreciated that variations of the described implementations and arrangements may be made without departing from the scope of the invention.

The invention claimed is:

1. A radiotherapy system comprising:
a first rotary support apparatus configured to support a radiation beam source and to cause the radiation beam source to rotate about a rotation axis;
a second rotary support apparatus;
a radiation shield mounted to the second rotary support apparatus, wherein the second rotary support apparatus is configured to cause the radiation shield to rotate about the rotation axis, and wherein the second rotary support apparatus includes one of:
a rotatable gantry, wherein the radiation shield is fixed to the rotatable gantry, and wherein the rotatable gantry is configured to rotate about the rotation axis passing through a center of the rotatable gantry;
two concentric ring gantries with concentric central bores centered on the rotation axis, wherein a first end and an opposing second end of the radiation shield are fixed to each of the two concentric ring gantries, and wherein the two concentric ring gantries are configured to rotate about the rotation axis to cause the radiation shield to rotate about the rotation axis; or
one or more curved guides, wherein the radiation shield is slidably mounted to the one or more curved guides to travel along the one or more curved guides.

2. The radiotherapy system of claim 1, further comprising:
the radiation beam source mounted to the first rotary support apparatus.

3. The radiotherapy system of claim 1, wherein the radiation shield is configured to be capable of rotating about the rotation axis independently of a rotation of the radiation beam source.

4. The radiotherapy system of claim 1, wherein the radiation shield is configured to rotate about the rotation axis in synchrony with a rotation of the radiation beam source.

5. The radiotherapy system of claim 1, further comprising:
a rotary drive system configured to drive the first rotary support apparatus that rotates at least one of the radiation beam source or the second rotary support apparatus radiation shield about the rotation axis.

6. The radiotherapy system of claim 1, wherein a rotation of the radiation beam source about the rotation axis causes the radiation shield to travel along a first curved path, the first curved path being along at least a portion of a circumference of a circle centered on the rotation axis, and wherein a rotation of the radiation shield about the rotation axis causes the radiation shield to travel along a second curved path, the second curved path being along at least a portion of a circumference of a circle centered on the rotation axis.

7. The radiotherapy system of claim 1, further comprising:
a fixed gantry with a central bore operable to receive the rotatable gantry of the second rotary support apparatus, wherein the rotatable gantry is rotatably mounted within the central bore of the fixed gantry and is configured to rotate with respect to the fixed gantry.

8. The radiotherapy system of claim 1, wherein the rotatable gantry is a drum gantry, and wherein the radiation shield is fixed inside the drum gantry.

9. The radiotherapy system of claim 1, wherein the radiation shield is fixed to an arm of the rotatable gantry extending outward from the rotatable gantry in an axial direction parallel to the rotation axis.

10. The radiotherapy system of claim 1, wherein the two concentric ring gantries are connected by one or more supporting beams that provide structural support to the two concentric ring gantries.

11. The radiotherapy system of claim 1, wherein each of the one or more curved guides is a circular ring centered on the rotation axis.

12. The radiotherapy system of claim 1, wherein each of the one or more curved guides forms a semicircle centered on the rotation axis.

13. The radiotherapy system of claim 1, wherein each of the one or more curved guides forms an arc of a circle centered on the rotation axis.

14. The radiotherapy system of claim 1, further comprising:
a second radiation shield slidably mounted to the one or more curved guides to travel along the one or more curved guides.

15. The radiotherapy system of claim 2, wherein the radiation beam source is configured to emit a beam of radiation directed towards the rotation axis.

16. The radiotherapy system of claim 4, further comprising:
a rotary coupling system configured to mechanically couple the rotation of the radiation beam source to the rotation of the radiation shield, wherein at least one of a rotation of the radiation shield drives a rotation of the radiation beam source or the rotation of the radiation beam source drives a rotation of the radiation shield using the rotary coupling system.

17. The radiotherapy system of claim 5, further comprising:
a control system configured to control the rotation of the radiation shield to cause the radiation shield to maintain a fixed position relative to the radiation beam source as the radiation beam source rotates about the rotation axis.

18. The radiotherapy system of claim 17, wherein the control system is configured to control the rotation of the radiation shield such that the radiation shield is always in a path of a radiation beam emitted from the radiation beam source as the radiation beam source rotates about the rotation axis.

19. The radiotherapy system of claim 17, wherein the control system is configured to control the rotation of the radiation shield such that the radiation shield is always diametrically opposed to the radiation beam source as the radiation beam source rotates about the rotation axis.

20. The radiotherapy system of claim 17, wherein the radiotherapy system further comprises:
a first rotary drive system configured to drive a rotation of the radiation beam source; and
a second rotary drive system configured to drive rotation of the radiation shield;
wherein the control system is configured to control one or both of the first rotary drive system and the second rotary drive system.

21. The radiotherapy system of claim 12, further comprising:
a fixed radiation shield extending between opposing ends of the one or more curved guides.

22. The radiotherapy system of claim 14, wherein the first shield apparatus is slidably mounted on a first portion of the one or more curved guides, and the second shield apparatus is slidably mounted on a second portion of the one or more curved guides.

23. The radiotherapy system of claim 22, wherein a position of the second shield apparatus on the second portion of the one or more curved guides is a reflection of a position of the first shield apparatus on the first portion, wherein the reflection is defined by a line of symmetry passing between the first and second portions of the one or more curved guides and through the rotation axis.

24. A method of controlling a rotation of a radiation shield in a radiotherapy system:
rotating a radiation beam source about a rotation axis, wherein the radiation beam source is mounted on a first rotary support apparatus and is configured to emit a radiation beam; and
rotating a radiation shield about the rotation axis, wherein the radiation shield is mounted on a second rotary support apparatus separate from the first rotary support apparatus, wherein the rotation of the radiation shield is synchronized with the rotation of the radiation beam source, and wherein the second rotary support apparatus includes one of:
a rotatable gantry, wherein the radiation shield is fixed to the rotatable gantry, and wherein the rotatable gantry is configured to rotate about the rotation axis passing through a center of the rotatable gantry;
two concentric ring gantries with concentric central bores centered on the rotation axis, wherein a first and an opposing second end of the radiation shield are fixed to each of the two concentric ring gantries, and wherein the two concentric ring gantries are configured to rotate about the rotation axis to cause the radiation shield to rotate about the rotation axis; or
one or more curved guides, wherein the radiation shield is slidably mounted to the one or more curved guides.

25. The method of claim 24, further comprising:
rotating the radiation shield about a second axis to maintain the radiation shield in a path of the radiation beam.

* * * * *